US006344574B1

(12) United States Patent
Foglia et al.

(10) Patent No.: US 6,344,574 B1
(45) Date of Patent: Feb. 5, 2002

(54) SOLVENT FRACTIONATION OF CHICKEN FAT FOR MAKING LIPID COMPOSITIONS ENRICHED IN UNSATURATED FATTY ACID-CONTAINING TRIACYLGLYCEROLS

(75) Inventors: Thomas A. Foglia, Lafayette Hill; Ki-Teak Lee, Philadelphia, both of PA (US); Donald D. Brillhart, Marshall, TX (US)

(73) Assignees: The United States of America as represented by the Secretary of Agriculture, Washington, DC (US); Lipotech, L.L.C., Cleveland, OH (US)

( * ) Notice: Subject to any disclaimer, the term of this patent is extended or adjusted under 35 U.S.C. 154(b) by 0 days.

(21) Appl. No.: 09/619,825

(22) Filed: Jul. 20, 2000

(51) Int. Cl.[7] ................................................. C07C 1/00

(52) U.S. Cl. ............................ 554/20; 554/8; 426/417; 426/425; 426/429

(58) Field of Search ....................... 554/8, 20; 426/417, 426/425, 429

(56) References Cited

PUBLICATIONS

Lee et al., Journal of Food Science, vol. 65, No. 5, pp. 826–831, 2000.*

Bockisch, Michael, Animal fats and oils, Fats and Oils Handbook, AOCS Press, Champaign, Illinois, 1998, Chapter 3, pp. 121–126, 156, & 172–173.

Brockerhoff, H., et al., Positional distribution of fatty acids in triglycerides of animal depot fats, Biochim. Biophys. Acta, 116 (1966), pp. 67–72.

Foglia, Thomas A., et al., Enzymatic interesterificationof tallow–sunflower oil mixtures, J. Am. Oil Chem. Soc., vol. 70, No. 3 (Mar. 1993), pp. 281–285.

Grundy, Scott M., Disorders of lipids and lipoproteins, Internal Medicine, Stein, ed., 2nd ed., 1987, pp. 2035–2050.

Halliwell, Barry, et al., Lipid peroxidation: a radical chain reaction, Free Radicals in Biology and Medicine, Clarendon Press–Oxford, 2nd ed., 1989, Chapter 4, pp. 188–276.

Lee, Ki–Teak, et al., Structured lipids: synthesis and applications, Food Rev. Int., 14(1), 1998, pp. 17–34.

Manganaro, F., et al., Acylglycerol structure of genetic varieties of Peanut oils of varying atherogenic potential, Lipids, vol. 16, No. 7 (1981), pp. 508–517.

Mattson, Fred H., et al., Comparison of effects of dietary saturated, mono–unsaturated, and polyunsaturated fatty acids on plasma lipids and lipoproteins in man, Journal of Lipid Research, vol. 26, 1985, pp. 194–202.

Nicolosi, Robert J., et al., Effect of dietary fat saturation on low density lipoprotein metabolism, Health Effects of Dietary Fatty Acids, Gary J. Nelson, ed., American Oil Chemists' Society, 1991, Chapter 7, pp. 77–82.

Spady, David K., et al., Dietary saturated triacylglycerols suppress hepatic low density lipoprotein receptor activity in the hamster, Proc. Natl. Acad. Sci. USA, vol. 82, Jul. 1985, pp. 4526–4530.

USDA, Livestock, Dairy and Poultry Situation and Outlook, Economic Research Service, U.S. Department of Agriculture, Washington, D.C., Publication #LDP–M–55, Jan. 26, 1999.

* cited by examiner

*Primary Examiner*—Deborah D. Carr
(74) *Attorney, Agent, or Firm*—Wood, Herron & Evans, L.L.P.

(57) ABSTRACT

Lipid compositions enriched in unsaturated fatty acid-containing triacylglycerols are made from chicken fat. The method involves solvent fractionation of chicken fat to provide a lipid composition containing enriched monounsaturated fatty acid esters (MUFAs) and polyunsaturated fatty acid esters (PUFAs).

30 Claims, 6 Drawing Sheets

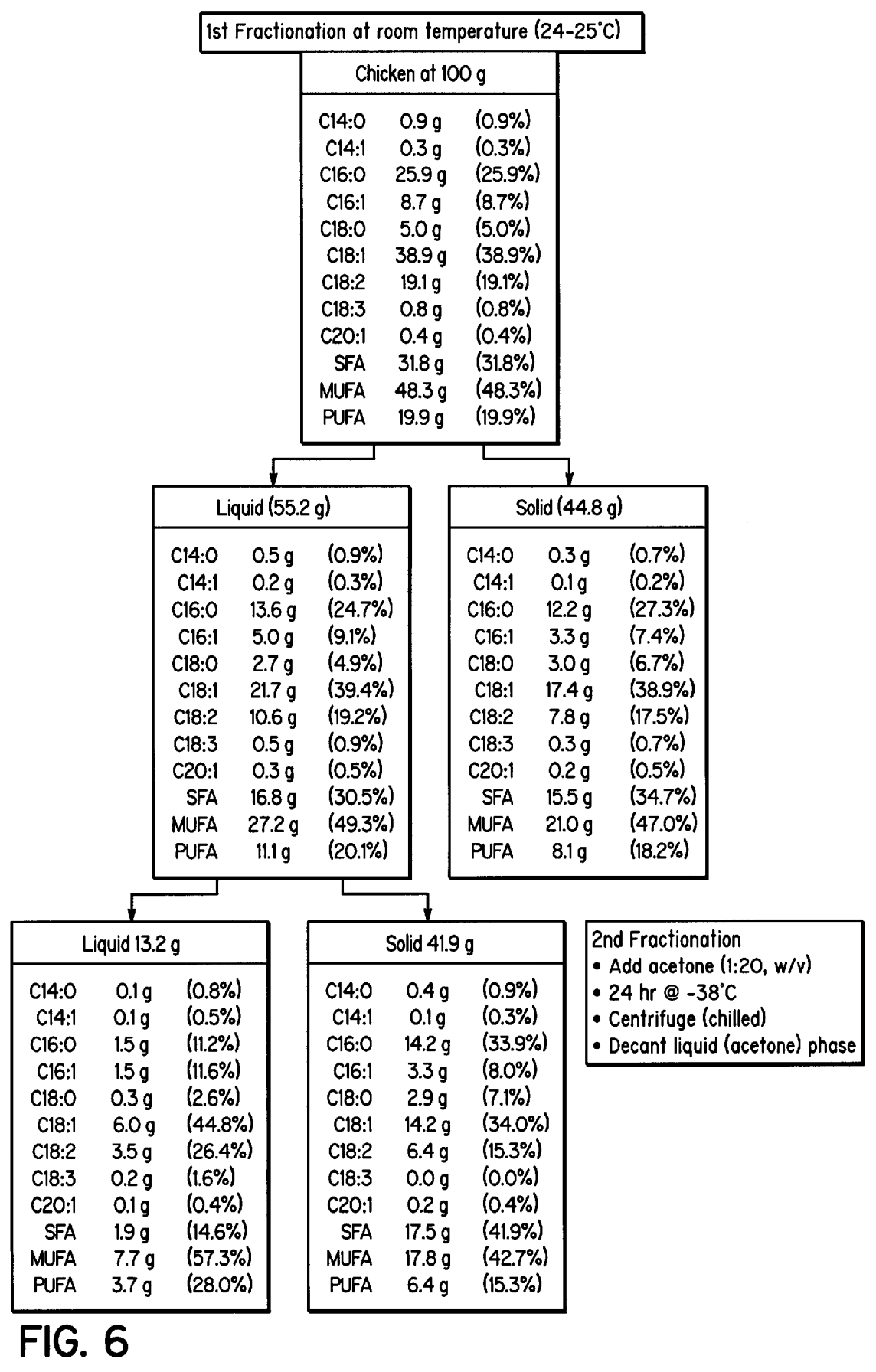

1st Fractionation at room temperature (24-25°C)

Chicken at 100 g

| | | |
|---|---|---|
| C14:0 | 0.9 g | (0.9%) |
| C14:1 | 0.3 g | (0.3%) |
| C16:0 | 25.9 g | (25.9%) |
| C16:1 | 8.7 g | (8.7%) |
| C18:0 | 5.0 g | (5.0%) |
| C18:1 | 38.9 g | (38.9%) |
| C18:2 | 19.1 g | (19.1%) |
| C18:3 | 0.8 g | (0.8%) |
| C20:1 | 0.4 g | (0.4%) |
| SFA | 31.8 g | (31.8%) |
| MUFA | 48.3 g | (48.3%) |
| PUFA | 19.9 g | (19.9%) |

Liquid (55.2 g)

| | | |
|---|---|---|
| C14:0 | 0.5 g | (0.9%) |
| C14:1 | 0.2 g | (0.3%) |
| C16:0 | 13.6 g | (24.7%) |
| C16:1 | 5.0 g | (9.1%) |
| C18:0 | 2.7 g | (4.9%) |
| C18:1 | 21.7 g | (39.4%) |
| C18:2 | 10.6 g | (19.2%) |
| C18:3 | 0.5 g | (0.9%) |
| C20:1 | 0.3 g | (0.5%) |
| SFA | 16.8 g | (30.5%) |
| MUFA | 27.2 g | (49.3%) |
| PUFA | 11.1 g | (20.1%) |

Solid (44.8 g)

| | | |
|---|---|---|
| C14:0 | 0.3 g | (0.7%) |
| C14:1 | 0.1 g | (0.2%) |
| C16:0 | 12.2 g | (27.3%) |
| C16:1 | 3.3 g | (7.4%) |
| C18:0 | 3.0 g | (6.7%) |
| C18:1 | 17.4 g | (38.9%) |
| C18:2 | 7.8 g | (17.5%) |
| C18:3 | 0.3 g | (0.7%) |
| C20:1 | 0.2 g | (0.5%) |
| SFA | 15.5 g | (34.7%) |
| MUFA | 21.0 g | (47.0%) |
| PUFA | 8.1 g | (18.2%) |

Liquid 13.2 g

| | | |
|---|---|---|
| C14:0 | 0.1 g | (0.8%) |
| C14:1 | 0.1 g | (0.5%) |
| C16:0 | 1.5 g | (11.2%) |
| C16:1 | 1.5 g | (11.6%) |
| C18:0 | 0.3 g | (2.6%) |
| C18:1 | 6.0 g | (44.8%) |
| C18:2 | 3.5 g | (26.4%) |
| C18:3 | 0.2 g | (1.6%) |
| C20:1 | 0.1 g | (0.4%) |
| SFA | 1.9 g | (14.6%) |
| MUFA | 7.7 g | (57.3%) |
| PUFA | 3.7 g | (28.0%) |

Solid 41.9 g

| | | |
|---|---|---|
| C14:0 | 0.4 g | (0.9%) |
| C14:1 | 0.1 g | (0.3%) |
| C16:0 | 14.2 g | (33.9%) |
| C16:1 | 3.3 g | (8.0%) |
| C18:0 | 2.9 g | (7.1%) |
| C18:1 | 14.2 g | (34.0%) |
| C18:2 | 6.4 g | (15.3%) |
| C18:3 | 0.0 g | (0.0%) |
| C20:1 | 0.2 g | (0.4%) |
| SFA | 17.5 g | (41.9%) |
| MUFA | 17.8 g | (42.7%) |
| PUFA | 6.4 g | (15.3%) |

2nd Fractionation

- Add acetone (1:20, w/v)
- 24 hr @ -38°C
- Centrifuge (chilled)
- Decant liquid (acetone) phase

FIG. 6

SOLVENT FRACTIONATION OF CHICKEN FAT FOR MAKING LIPID COMPOSITIONS ENRICHED IN UNSATURATED FATTY ACID-CONTAINING TRIACYLGLYCEROLS

FIELD OF THE INVENTION

The present invention pertains to enriched unsaturated fatty acid-containing triacylglycerols and a method of making them employing chicken fat. In particular, the method involves the solvent fractionation of chicken fat to provide a lipid composition containing enriched amounts of unsaturated fatty acid esters (UFA or UFAs) including monounsaturated fatty acid esters (MUFA or MUFAs) and polyunsaturated fatty acid esters (PUFA or PUFAs).

BACKGROUND OF THE INVENTION

One established approach to reducing plasma cholesterol levels is to consume a large proportion of dietary triglycerides as polyunsaturated fatty acid (PUFA) derivatives. The most widely occurring dietary PUFA is linoleic acid (C18:2n-6, or 9,12-octadecadienoic acid), which constitutes more than half of the fatty acid triglycerides of corn, soy, and safflower vegetable oils. The cholesterol lowering ability of PUFAs is believed to result from increased LDL receptor activity. See Shady & Dietschy, 82 Proc. Nat. Acad. Sci. USA 4576 (1985). This well established lowering of plasma LDL cholesterol concentration when PUFAs are substituted for dietary saturated fatty acids (hereinafter SFA or SFAs) provides the rationale for the widespread substitution of a variety of vegetable oils for animal fats in cooking and food formulations. The American Heart Association in its Phase I and Phase II Recommended Diets has approved the use of PUFAs as part of a large scale dietary modification for the purpose of lowering cholesterol levels in the general population. See, e.g., S. M. Grundy, Disorders of Lipids and Lipoprotein, in *Internal Medicine*, Stein, ed. 2035–2046 ($2^{nd}$ ed. 1987).

However, PUFAs have significant deleterious health consequences as well as beneficial ones. Several negative effects of PUFAs may be ascribed to their increased rate of reaction via free-radical mechanisms. See, e.g., B. Hall and J. Gutteridge, "Lipid Peroxidaton," Ch. 4 in *Free Radicals in Biology and Medicine*, (2d ed. 1989). PUFAs usually have two vinylic groups separated by a methylene carbon, as is exemplified by the 9,12 diene structure of linoleic acid. Their susceptibility to peroxidation and cross-linking reactions implicates PUFAs in several undesirable processes such as tissue aging, tumorigenesis and lowering the level of beneficial HDL cholesterol as well as the level of harmful LDL cholesterol.

Monounsaturated fatty acids, such as oleic acid (C18:1n-9) or (cis-9-octadecenoic acid), are known to reduce blood cholesterol levels in non-hypertriglyceridemic individuals (Mattson, F. H. and Grundy, S. M. 1985 J. Lipid Res. 26:194–202). Among vegetable oils, those of olive, peanut, rapeseed and canola have been identified as being rich sources of MUFA, with the latter type fatty acids constituting from 50% to 80% of their fatty acid composition. Because of the importance placed on dietary MUFA, it has been recommended that MUFA intake be as high as half of the total recommended dietary intake of calories from fat (30%) as a means for reducing the risk of coronary artery disease (Nicolosi, R. J., Stucchi, A. F., and Loscalzo, J. 1991. Chapter 7 in *Health Effects of Dietary Fatty Acids*, G. J. Nelson (Ed.), p 77–82, AOCS Press, Champaign, IL; Bockisch, M. 1998. In Fats and Oils Handbook, AOCS Press, Champaign, Ill.; Lee, K- T. and Akoh, C. C. 1998a. Food Rev. Int. 14:17–34).

Although scientifically based claims of health benefits derived from dietary MUFAs previously have been asserted for oleic acid, other monounsaturated fatty acids also occur naturally. The most common are 11-eicosenoic acid (C20:1n-9) and 13-docosenoic acid (C22:1n-9), both of which are found in high levels in some oilseed plants such as jojoba and rapeseed. The shorter chain MUFA 9-palmitoleic acid (C16:1n-7) occurs as a minor component (ca. 2%) in olive and cottonseed oils and in trace amounts in a few other commercially available vegetable oils. Palmitoleic acid occurs in somewhat high amounts in animal fat triglycerides such as lard and tallow (up to 5%) and in still higher levels in some fish oils such as sardine oil. The next lower homologue, myristoleic (9-tetradecenoic) acid (C14:1n-5), occurs in minor amounts in animal fat and in butter. The even lower homologue, lauroleic (9-dodecenoic) acid (C12:1n-3), occurs rarely and in small amounts in natural sources.

Several animal fats contain short chain MUFAs in sufficiently high proportions to make them good starting materials for formulating desirable compositions. Chicken and turkey fats, beef tallow, and foot bone oil triglycerides contain C16:1n-7 in amounts of about 4–6% by weight. Some fish oils such as sardine and menhaden may contain as much as 10–16% C16:1n-7. Whale oil is reported to contain above 13% C16:1n-7, and the now unavailable sperm whale oil contained up to 26%. However, these fats and oils as rendered from the natural sources contain undesirably large relative proportions of the long chain fatty acids of the series C20: x and above. The more saturated and higher melting members C20:0, C20:1 and C22:0 have been reported to contribute to the high atherogenicity of peanut oil, a phenomenon comprehensible in light of the teachings of this patent. See F. Manganaro, et al., 16 Lipids 508 (1981). The polyunsaturated and lower melting members C20:2, C20:3, C20:4, C20:5, C22:2, C22:3, C22:4, C22:5, and C22:6 are non-atherogenic or even cardioprotective, but are highly sensitive to free radical oxidation and cross linking reactions because of their polyunsaturation.

The principal source of a dietary vegetable oil which contains appreciable amounts of C16:1n-7 is macadamia nuts. The two species, integrifolia and tetrafolia, contain C16:1n-7 in amounts ranging from 16 to 25% (w/w) of the fatty acids in the oil. However, both also contain about 2% to 4% C20 fatty acids. In addition, the other fatty acids of macadamia nut oil are closely similar in both identity and quantity to those present in olive oil.

Similarly, some natural fats and oils are acceptable starting materials from which to manufacture desirable compositions, that is, an oil enriched in the other selected short chain MUFAs. For example, tallow contains about 0.5% C14:1n-5. It also contains about 1% or more C20 to C22 fatty acids. Butterfat contains very large proportions, up to 3%, of C14:1n-5. However, butterfat has other lipid components, including a large fraction of C4 to C10 fatty acids. The latter are metabolized by a quite different pathway from the C12 and longer fatty acids. Butterfat also contains greater than 2% C20 fatty acids.

In U.S. Pat. No. 5,198,250, food and pharmaceutical compositions containing short chain monounsaturated fatty acids (MUFAs) and methods of using them are disclosed. In particular, as set forth in detail in that patent, MUFA compositions were formulated to produce beneficial improvements in the metabolic processing of lipids or glucose in animals to which the compositions of matter are regularly administered. Beneficial improvements in the metabolic processing of lipids are evidenced by different effects in various tissues. Generally, the metabolic processing of lipids may include any or all steps in the metabolic pathways which include, in part, lipid uptake from dietary sources, hydrolysis, esterification of fatty acids to produce other lipid species, packaging of lipids into lipoproteins, lipid transport, lipid storage in tissues, lipid or lipoprotein cellular uptake, lipid synthesis, enzymatic modification and catabolism, and pathological lipid deposition in arteries, liver, heart and in adipose tissue. As set forth in the disclosure of that patent in detail, regular or systematic administration of the formulated MUFA compositions provide beneficial improvements in metabolic processing.

In 1998, chicken was the most produced and consumed meat in the United States (USDA 1999. Publication #LDP-M-55, Economic Research Service, Washington, D.C.). Despite its production and ready availability as a coproduct of chicken production, chicken fat, unlike beef tallow, is usually not used separately in other food or non-food uses. However, animal fats, in general, are of dietary concern because of their relatively high long-chain (C16 and C18 carbon atoms) saturated fatty acid (SFA) content. Chicken fat can be considered a source of MUFA since they constitute 45–50% of chicken fat fatty acids, while tallow contains only 30–40% MUFA (Brockerhoff, H., Hoyle, R. J., and Wolmark, N. 1966. Biochem. Biophys. Acta 116:67–72.; Bockisch, M. 1998. In *Fats and Oils Handbook*, AOCS Press, Champaign, Ill.).

In brief, MUFAs selected from the group composed of palmitoleic acid (C16:1) and its positional isomers, myristoleic (tetradecenoic) acid (C14:1) and its positional isomers and lauroleic (dodecenoic) acid (C12:1), or their mixtures, whether as free acids, salts or esters thereof, are known to provide improvements in the metabolic processing of lipids. However, natural sources for such MUFAs, such as macadamia nut oil, are in limited supply. In order to satisfy the demands for MUFAs, especially to provide new sources for such MUFA compositions, improved methods are needed. Furthermore, new lipid compositions of UFAs containing PUFAs and MUFAs are needed.

SUMMARY OF THE INVENTION

This invention is directed to a method of making a lipid composition enriched in unsaturated fatty acid esters from chicken fat. According to the method, chicken fat is solvent fractionated to produce lipid fractions that are enriched in unsaturated fatty acid-containing triacylglycerols. The fractionated lipid composition has an increased amount of unsaturated fatty acid esters and a decreased amount of saturated fatty acid esters compared to their original amounts in the chicken fat.

According to one preferred method of the invention, chicken fat is solvent fractionated with a solvent, such as acetone, and the fractionation is conducted at a low temperature, preferably below ambient temperature, or below 0° C. to −15° C., and, more preferably, about −18° C. to about −40° C. In another form of the method, the chicken fat may be first prewarmed, for example, at about 60° C. for a sufficient period of time and then dry-fractionated at room or ambient temperature during which time liquid and solid phases are formed. The separated liquid phase is then solvent-fractionated with a suitable solvent, such as acetone, at low temperatures on the order of about 0° C. to about −40° C.

The unsaturated fatty acid-containing triacylglycerols enriched fractions produced by the method have significantly increased amounts of PUFAs and MUFAs. For instance, solvent fractionations at about −18° to about −38° C. produced lipid compositions having about 14 to 34% by weight more UFAs compared to the original amounts of UFAs in the chicken fat. In contrast, saturated fatty acids (SFAs) in the fractionated lipids decreased to about 40% to 74% by weight of the original SFAs present in the chicken fat. Correspondingly, the MUFAs in the fractionated lipid compositions increased about 16% to 20% by weight of their original amounts.

When the two-step process is used which requires separation of a liquid phase of the fat be dry-fractionated at ambient temperatures, preferably about 0° C. to 35° C., prior to solvent-fractionation, less solvent may be employed. According to this two-step process, when solvent-fractionation at low temperatures on the order of about −18° C. to about −38° C. is conducted, the UFAs increased in the fractionated lipid composition to about 19% to 25%, and the SFAs decreased to about 41% to 54%; and the MUFAs increased to about 19% to 21% by weight. Thus, the two-step method produces the similar advantage of enrichment in UFAs and particularly MUFAs with a significant decrease in SFAs compared to the original chicken fat compositions.

In summary, novel lipid compositions are produced by the method of this invention. These compositions provide a number of advantages. For example, the content of the MUFAs in the lipid compositions are increased with a significant decrease of SFAs. An increase of the ratio of the unsaturated to the saturated fatty acids is also provided. The method offers an overall natural product for human consumption to facilitate the metabolic processing of lipids and avoid unwanted lipid deposits.

Other benefits and advantages of this invention will be further understood with reference to the following detailed description and examples.

BRIEF DESCRIPTION OF THE FIGURES

FIGS. 1–6 are diagrammatic flow charts of the fractionation of chicken fat and show chicken fat having original summed (Σ) amounts of ΣSFA, ΣMUFA and ΣPUFA which have been solvent fractionated into liquid fractions containing unsaturated fatty acid enriched triacylglycerols.

DETAILED DESCRIPTION

With reference to FIGS. 1–6 and the following detailed Examples 1–2, chicken fat was fractionated by a single-step solvent fractionation and a two-step solvent fractionation as referred to above. According to FIGS. 1–3 and Example 1, chicken fat was solvent fractionated by the single-step method at low temperatures on the order of about −18° C. to about −38° C. While acetone is employed in accordance with the preferred best current mode of the invention, in its broader aspects, other solvents may be employed for the fractionation such as isopropanol, hexane, ethanol and isooctane. The alcohols include $C_{1-8}$ alcohols, preferably ethanol and isopropanol. The amount of solvent generally is about 5 to 40 volumes of solvent to 1 gram of fat and in the examples which follow, a ratio of 20 volumes per 1 gram of fat was used. Furthermore, while the most preferred low temperature solvent fractionations are conducted at about −18° C. to about −38° C., in its broader aspects, low temperatures below about 0° C. to −15° C. may be employed, or within the range of 0° C. to −40° C. It has been found that the lower temperatures produce more preferred results. For instance, the total saturated fatty acids (Σ SFAs) are decreased in the liquid lipid fraction about 30% to 75% by weight of the original amounts in the fat as the temperature is decreased. Furthermore, as the temperature is decreased, the enriched amounts of total MUFAs (Σ MUFAs) in the liquid lipid fraction increased about 16% to 20% by weight of the original amounts in the fat. Overall, according to the single-step method, Σ UFAs are enriched in the liquid lipid fraction about 15–35% by weight, whereas Σ SFAs are decreased about 30% to 75% by weight, compared to their original amounts in the fat.

Figure 4:
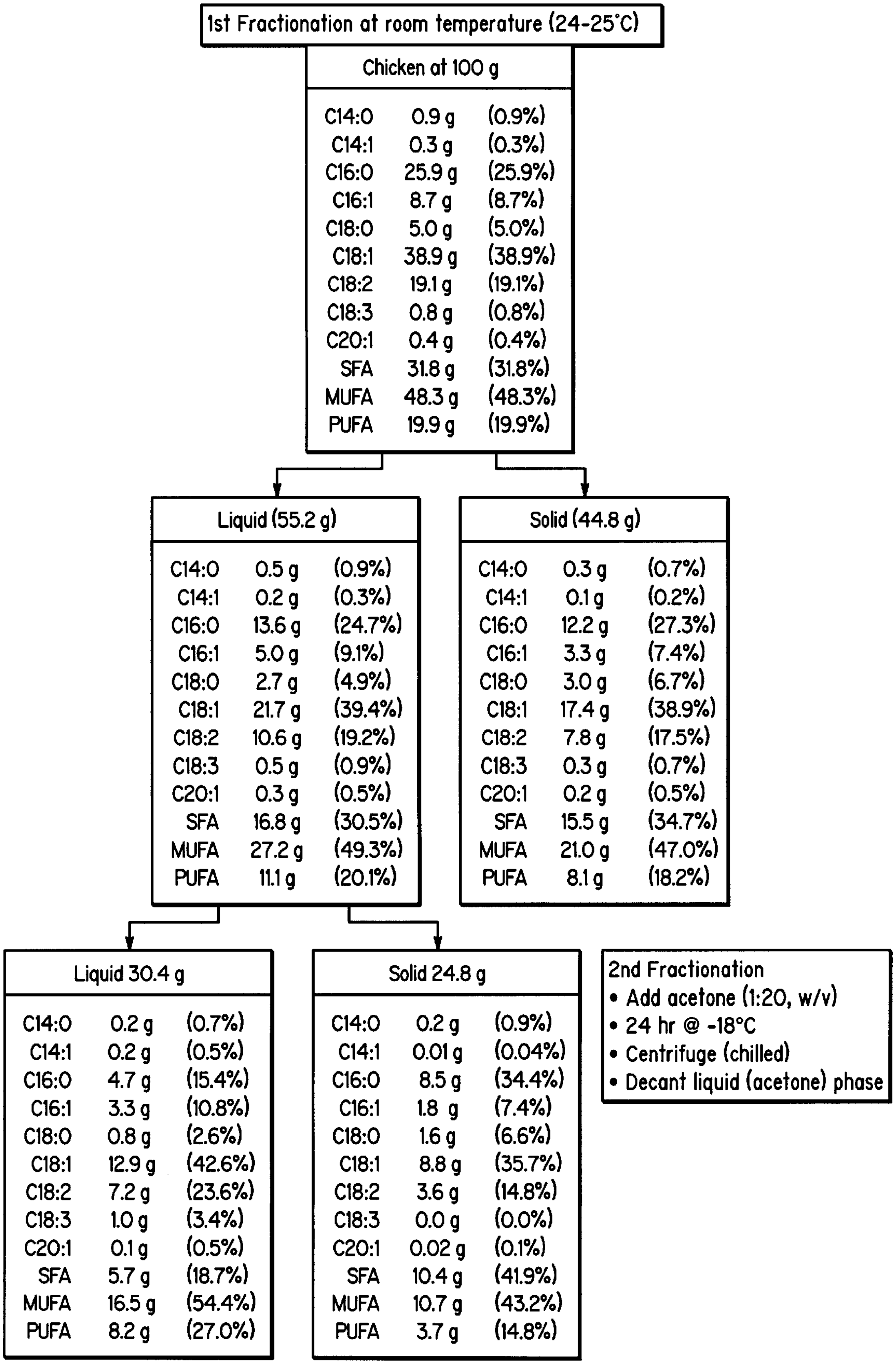
Figure 5:
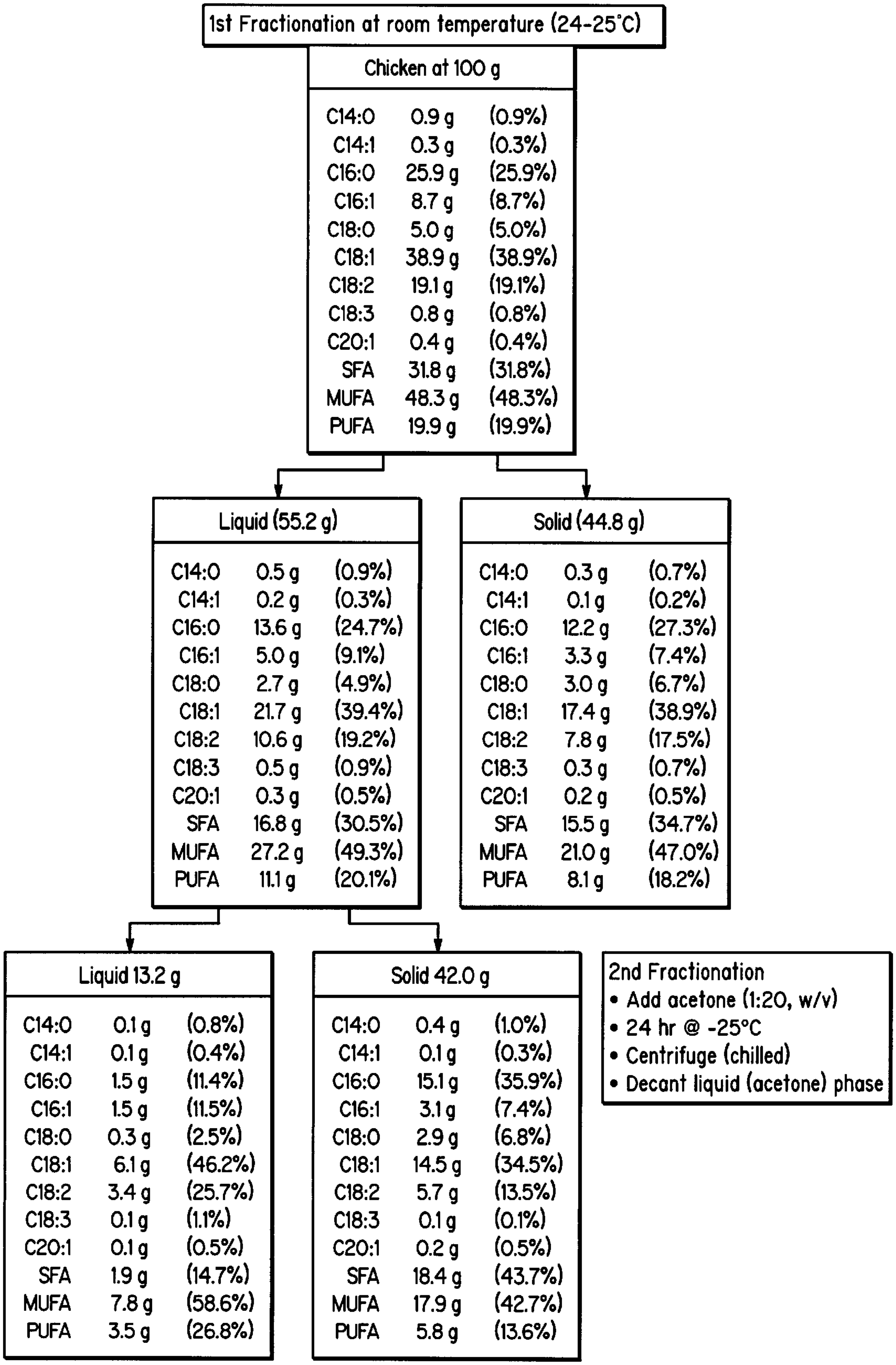

According to the two-step method with reference to FIGS. 4–6 and Example 2, less solvent is needed to provide a solvent fractionation of the liquid fraction which has been separated by pre-warming of the fat followed by dry-fractionation of the solid and liquid fractions, and then solvent-fractionation of the liquid fraction. According to this two-step method, there is still a significant decrease in Σ SFAs of about 41–54% by weight in the liquid lipid fraction. Correspondingly, there are significant increases in Σ UFAs of about 19% to about 25% by weight as the temperature is decreased in the second step of solvent fractionation.

EXAMPLE 1

Single-Step Fractionation of Chicken Fat

Pre-warmed (60° C. for 20 min) chicken fat (100 g, obtained from Tyson Foods, Inc., Springdale, Ariz.) was divided into 2 g aliquots, each of which was placed in 50-ml polypropylene centrifuge tubes. Twenty volumes (20 ml/gram) of HPLC analytical grade acetone (obtained from Baxter Health Corp., Muskegon, Mich.) were added to each tube, the contents were thoroughly vortex-mixed, and were held at one of three temperatures (−19° C., −25° C., or −38° C.) for 24 hr. For all fractionations, each tube was placed in a 250-ml insulated wide-mouth centrifuge tube to minimize temperature changes during centrifugation. After centrifugaton (2300×g for 15 min) in a pre-chilled Sorvall RC5B centrifuge, the liquid and solvent phases were separated by decantation. The liquid fractions were pooled, as were the solid pellets. Acetone was evaporated from the pooled fractions at 60° C. under nitrogen gas, and aliquots of the acetone-free pooled liquid and solid fractions were reserved for analysis. The pooled liquid fractions are fit for human consumption according to the Code of Federal Regulations, 21 CFR 173.210.

All fractions were converted to fatty acid methyl esters (FAME) with 14% boron trifluoride in methanol as described previously by Foglia et al (J. Am. Oil Chem. Soc., 70, 281–285, 1993). FAME compositions were determined with a Hewlett Packard Model 5890 Series II gas chromatograph equipped with a split automatic injector, a flame ionization detector, and a HP-INNOWAX column (30×0.25 mm i.d., 53 $\mu$m film thickness, obtained from Hewlett-Packard, Wilmington, Del.). The column was held at 120° C. for 2 min then programmed to 230° C. at a rate of 5° C./min and held at final temperature for 22 min. The injector and detector temperatures were 260° C. and the carrier gas was helium at a flow of 5.5 ml/min. A Hewlett Packard Model 5890 Series II gas chromatograph with a HP Mass Selectrive Detector (MSD) Model 5972 series was used for identification of FAME. The MSD was scanned from m/z 10 to m/z 600 at 1.2 scans/sec. A HP-5 capillary column (30×0.25 mm i.d., 25 $\mu$m film thickness) was used to separate FAME. The column was held at 80° C. for 2 min and programmed to 230° C. at a rate of 10° C./min. The injector and detector temperatures were 230° C. and 280° C., respectively.

Figure 1:
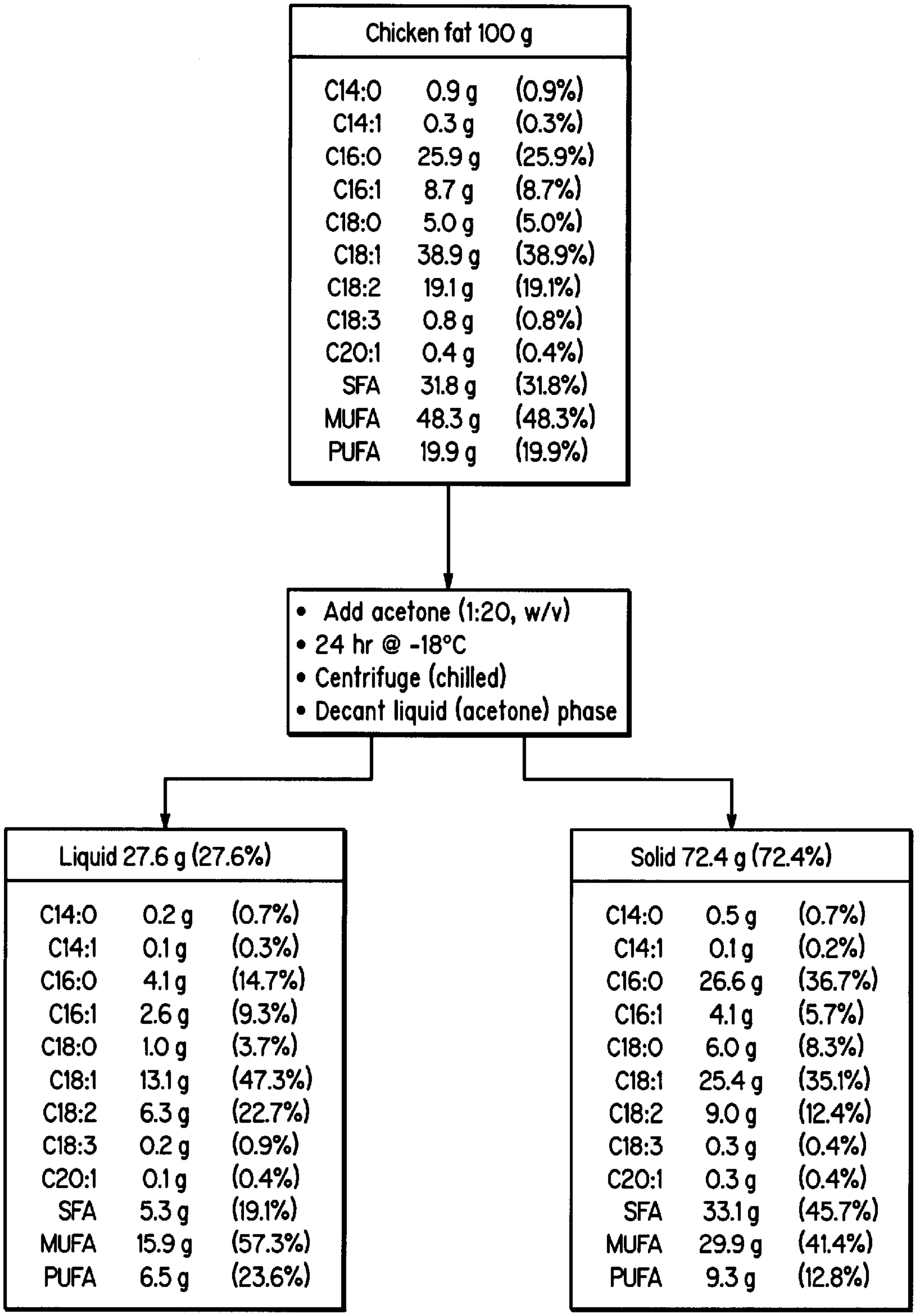

FIG. 1 shows the fatty acid composition of each phase when the fractionation was performed at −18° C. Fractionation yielded a liquid fraction of 27.6 g (27.6%) and a solid phase of 72.4 g (72.4%). The percentage concentration of palmitoleic acid (C16:1) in the chicken fat starting material (8.7%) was increased to 9.3% in the liquid fraction. The combined saturated fatty acids (ΣSFA; C14:0, C16:0 and C18:0) in chicken fat (31.8%) were decreased to 19.1% in the liquid fraction. The combined monounsaturated fatty acids (ΣMUFA; C14;1, C16:1, C18:1 and C20:1) in chicken fat (48.3%) were increased to 57.3% in the liquid fraction. The combined polyunsaturated fatty acids (ΣPUFA; C18:2 and C18:3) in chicken fat (19.9%) were increased to 23.6% in the liquid fraction.

Figure 2:
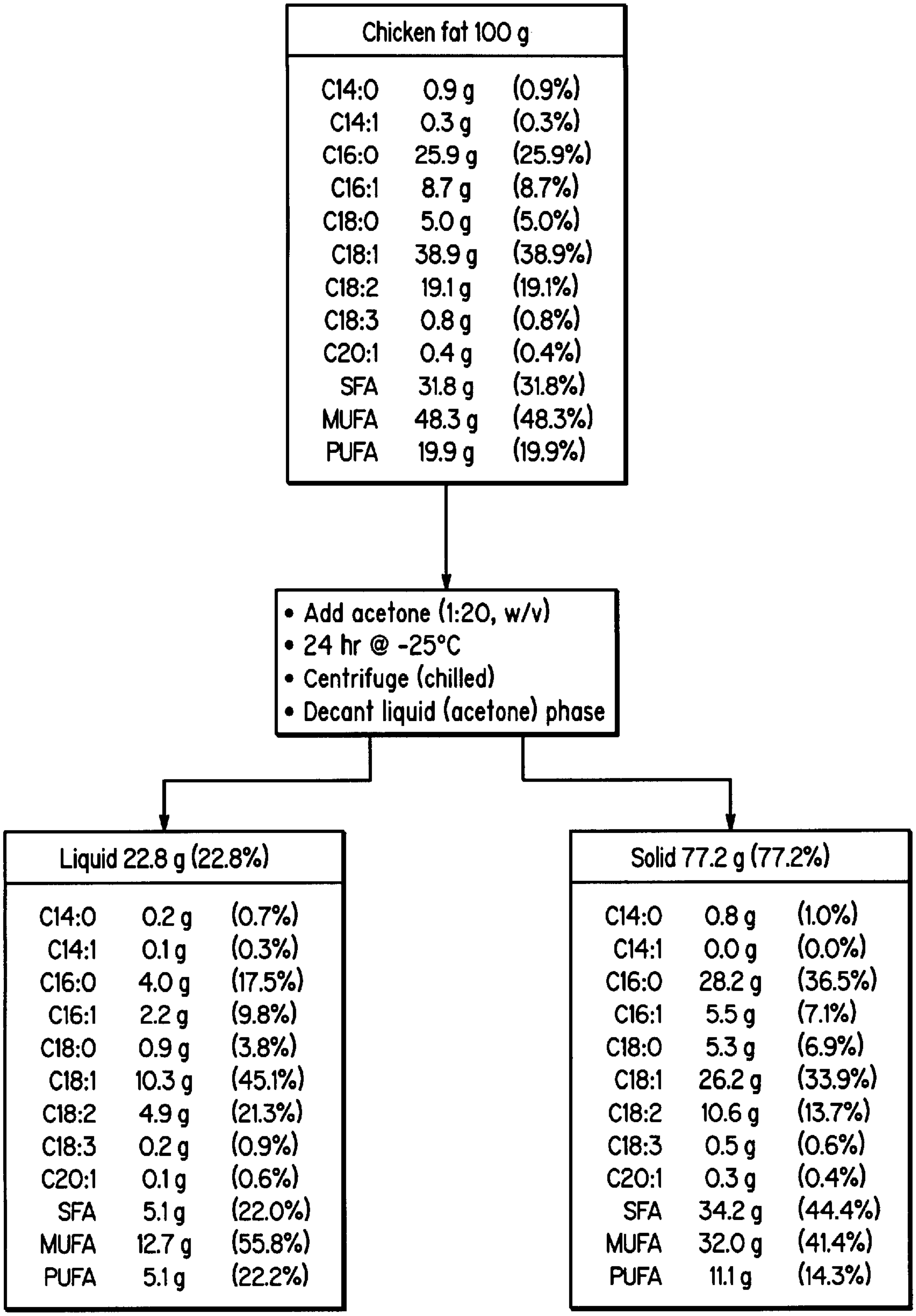

FIG. 2 shows the fatty acid composition of each phase when the fractionation was performed at −25° C. Fractionation yielded a liquid fraction of 22.8 g (22.8%) and a solid fraction of 77.2 g (77.2%). The percentage concentration of palmitoleic acid (C16:1) in the chicken fat starting material (8.7%) was increased to 9.8% in the liquid fraction. The ΣSFA in chicken fat were decreased to 22.0% in the liquid fraction. The ΣMUFA in chicken fat were increased to 55.8% in the liquid fraction. The ΣPUFA in chicken fat were increased to 22.2% in the liquid fraction.

Figure 3:
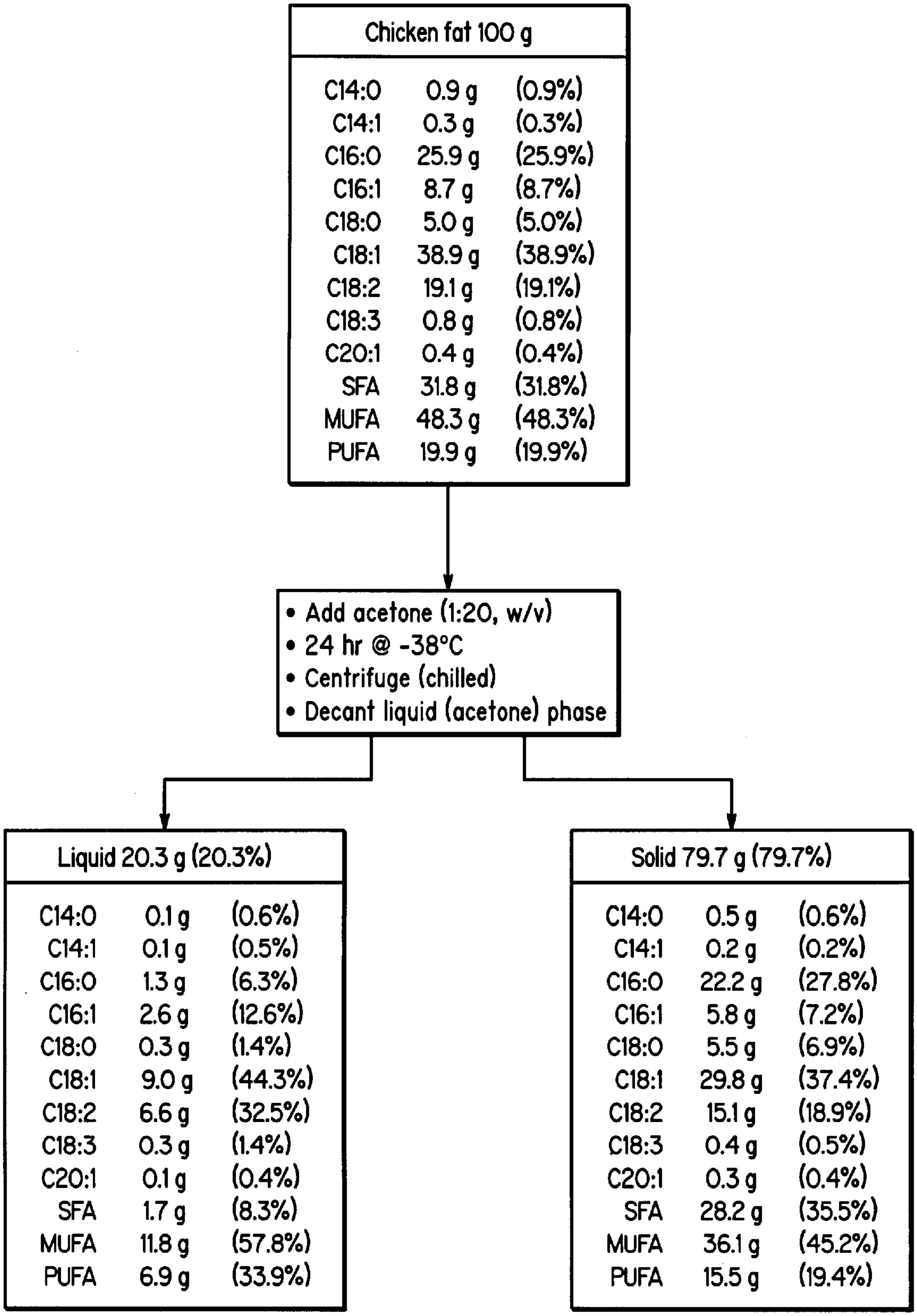

FIG. 3 shows the fatty acid composition of each phase when the fractionation was performed at −38° C. Fractionation yielded a liquid fraction of 20.3 g (20.3%) and a solid fraction of 79.7 g (79.7%). The percentage concentration of palmitoleic acid (C16:1) in the chicken fat starting material (8.7%) was increased to 12.6% in the liquid fraction. The ΣSFA in chicken fat were decreased to 8.3% in the liquid fraction. The ΣMUFA in chicken fat were increased to 57.8% in the liquid fraction. The ΣPUFA in chicken fat were increased to 33.9% in the liquid fraction.

EXAMPLE 2

Two-Step Fractionation of Chicken Fat

Pre-warmed (60° C. for 20 min) chicken fat (100 g, obtained from Tyson Foods, Inc., Springdale, Ariz.) was in a 250-ml polypropylene centrifuge tube and dry-fractionated at room temperature (24–25° C.) for 24 hr. during which time the liquid and solid fractions naturally separated due to their mutual solvent characteristics. The liquid phase (55.2 g) was separated from the solid phase (44.8 g) by decantation, and 1-g aliquots of each were reserved for analysis. The liquid phase (54.2 g) was divided into 2-g aliquots, each of which was placed in a 50-ml polypropylene centrifuge tube. Twenty volumes (20 ml/gram) of HPLC analytical grade acetone (obtained from Baxter Health Corp., Muskegon, Mich.) were added to each tube, the contents were thoroughly vortex-mixed, and were held at one of three temperatures (−18° C., −25° C., or −38° C.) for 24 hr. For all fractionations, the liquid and solvent phases were simply separated by decantation after crystallization in acetone. The liquid fractions were pooled, as were the solid pellets. Acetone was evaporated from the pooled fractions at 60° C. under nitrogen gas, and 1-g aliquots of the acetone-free pooled liquid and solid fractions were reserved for analysis.

All fractions were converted to fatty acid methyl esters (FAME) with 14% boron trifluoride in methanol as described previously by Foglia et al (J. Am. Oil Chem. Soc., 70, 281–285, 1993). FAME compositions were determined with a Hewlett Packard equipment as described above in Example 1.

FIG. 4 shows the fatty acid composition of each fraction when the second fractionation was performed at −18° C. The first fractionation yielded a liquid fraction of 55.2 g (55.2%)

and a solid faction of 44.8 g (44.8%), and the second fractionation yielded a liquid fraction of 30.4 g (55.1%) and a solid fraction of 24.8 g (44.9%). The percentage concentration of palmitoleic acid (C16:1) in the chicken fat starting material (8.7%) was increased to 9.1% in the liquid fraction prepared at room temperature, and increased further to 10.8% in the second liquid fraction prepared at −18° C. The combined saturated fatty acids (ΣSFA; C14:0, C16:0 and C18:0) in chicken fat (31.8%) were decreased to 30.5% in the first liquid fraction and were further decreased to 18.7% in the second liquid fraction. The combined monounsaturated fatty acids (ΣMUFA; C14;1, C16:1, C18:1 and C20:1) in chicken fat (48.3%) were increased to 54.4% in the liquid fraction. The combined polyunsaturated fatty acids (ΣPUFA; C18:2 and C18:3) in chicken fat (19.9%) were increased to 20.1% in the first liquid fraction and were further increased to 27.0% in the second liquid fraction.

FIG. 5 shows the fatty acid composition of each fraction when the second fractionation was performed at −25° C. The first fractionnation yielded a liquid fraction of 55.2 g (55.2%) and a solid fraction of 44.8 g (44.8%), and the second fractionation yielded a liquid fraction of 13.2 g (24.4%) and a solid fraction of 42.0 g (77.6%). The percentage concentration of palmitoleic acid (C16:1) in the chicken fat starting material (8.7%) was increased to 9.1% in the liquid fraction prepared at room temperature, and increased further to 11.5% in the second liquid fraction prepared at −25° C. The ΣSFA in chicken fat were decreased to 30.5% in the first liquid fraction and were further decreased to 14.7% in the second liquid fraction. The ΣMUFA in chicken fat were increased to 49.3% in the first liquid fraction and were further increased to 58.6% in the second liquid fraction. The ΣPUFA in chicken fat were increased to 20.1% in the first liquid fraction and were further increased to 26.8% in the second liquid fraction.

FIG. 6 shows the fatty acid composition of each fraction when the second fractionation was performed at −38° C. The first fractionation yielded a liquid fraction of 55.2 g (55.2%) and a solid fraction of 44.8 g (44.8%), and the second fractionation yielded a liquid fraction of 13.3 g (24.1%) and a solid fraction of 49.1 g (75.9%). The percentage concentration of palmitoleic acid (C16:1) in the chicken fat starting material (8.7%) was increased to 9.1% in the liquid fraction prepared at room temperature, and increased further to 11.6% in the second liquid fraction prepared at −38° C. The ΣSFA in chicken fat were decreased to 30.5% in the first liquid fraction and were further decreased to 14.6% in the second liquid fraction. The ΣMUFA in chicken fat were increased to 49.3% in the first liquid fraction and were further increased to 57.3% in the second liquid fraction. The ΣPUFA in chicken fat were increased to 20.1% in the first liquid fraction and were further increased to 28.0% in the second liquid fraction.

The following TABLE illustrates in summary form the relative increased amounts of unsaturated fatty acid esters and decreased amounts of saturated fatty esters in the liquid fractions of the lipid compositions relative to their original amounts in the chicken fat prior to the single- and two-step processes of FIGS. 1–6. The original total amounts (Σ) by weight of the SFAs, UFAs and MUFAs in the chicken fat were 31.8%, 68.2% and 48.3%, respectively. The TABLE gives the relative percents of ΣSFAs, ΣUFAs and ΣMUFAs in the liquid fractions of lipid and the approximate percentage decrease (−) or increase (+) compared to their original amounts in the chicken fat. These results tabulate the overall improvements achieved according to the methods of this invention.

TABLE

| | |
|---|---|
| FIG. 1 | at −18° C., single-step<br>Σ SFAs = 19.1 (−40%)<br>Σ UFAs = 80.9 (+19%)<br>Σ MUFAs = 57.3 (+16%) |
| FIG. 2 | at −25° C., single-step<br>Σ SFAs = 22.0 (−31%)<br>Σ UFAs = 78.0 (+14%)<br>Σ MUFAs = 55.8 (+16%) |
| FIG. 3 | at −38° C., single-step<br>Σ SFAs = 8.3 (−74%)<br>Σ UFAs = 91.7 (+34%)<br>Σ MUFAs = 57.8 (+20%) |
| FIG. 4 | at −18° C., two-step<br>Σ SFAs = 18.7 (−41%)<br>Σ UFAs = 81.4 (+19%)<br>Σ MUFAs = 54.4 (+13%) |
| FIG. 5 | at −25° C., two-step<br>Σ SFAs = 14.7 (−54%)<br>Σ UFAs = 85.4 (+25%)<br>Σ MUFAs = 58.6 (+21%) |
| FIG. 6 | at −38° C., two-step<br>Σ SFAs = 14.6 (−54%)<br>Σ UFAs = 85.3 (+25%)<br>Σ MUFAs = 57.3 (+19%) |

In view of the above detailed description, it will become apparent to those of ordinary skill in the art that other variations of the method and compositions may be made without departing from the sprit and scope of this invention.

What is claimed is:

1. A method of making a lipid composition enriched in unsaturated fatty acid esters from chicken fat comprising providing chicken fat having original amounts of unsaturated fatty acid esters and saturated fatty acid esters, mixing said chicken fat with solvent to fractionate said fat, maintaining said mixture at a temperature and for a sufficient time to facilitate said solvent fractionation of a lipid composition having an increased amount of said unsaturated fatty acid esters and a decreased amount of said saturated fatty acid esters relative to said original amounts, and isolating the lipid composition enriched in said unsaturated fatty acid esters.

2. The method of claim 1 comprising the further step of separating said chicken fat into a solid phase and liquid phase by dry-fractionation prior to mixing the liquid phase with solvent for said fractionation.

3. The method of claim 2 wherein the chicken fat is heated to an elevated temperature for liquification prior to said dry-fractionation at about 0° C. to 35° C.

4. The method of claim 1 wherein the solvent is selected from the group consisting of acetone, isopropanol, hexane, ethanol and isooctane.

5. The method of claim 1 wherein the solvent is acetone.

6. The method of claim 1 wherein said solvent fractionation is conducted at a temperature below about 0° C. to about −15° C.

7. The method of claim 1 wherein said solvent fractionation is conducted at a temperature of about 0° C. to about −40° C.

8. The method of claim 1 wherein said solvent fractionation produces a liquid fraction and a solid fraction followed by separating the liquid fraction containing the lipid composition from the solid fraction by centrifugation.

9. The method of claim 8 comprising the further step of removing solvent from said lipid composition to a level fit for human consumption.

10. The method of claim 8 wherein the liquid fraction is separated from the solid fraction by centrifugation at a temperature below about 0° C. to about −15° C.

11. The method of claim 8 wherein said liquid fraction is separated from the solid fraction by centrifugation at a temperature of from about 0° C. to about −40° C.

12. The method of claim 1 wherein said unsaturated fatty acid esters are selected from the group consisting of C14:1, C16:1, C18:1, C18:2, C18:3, and C20:1, and mixtures thereof.

13. The method of claim 12 wherein the monounsaturated fatty esters consist mainly of C16:1 and C18:1.

14. The method of claim 1 wherein said lipid composition has an amount of unsaturated fatty acid esters which is increased about 19% to 34% and an amount of saturated fatty acid esters which is decreased about 30% to about 74%, both amounts relative to their original amounts.

15. The method of claim 14 wherein said unsaturated fatty acid esters contain monounsaturated fatty acid esters in an amount from about 16% to about 20% relative to original amounts of monounsaturated fatty acid esters in the chicken fat.

16. A method of making a lipid composition enriched in unsaturated fatty acid esters from chicken fat comprising providing chicken fat having original amounts of unsaturated fatty acid esters and saturated fatty acid esters, mixing said chicken fat with acetone to fractionate said fat, maintaining said mixture at a temperature of ambient temperature to −40° for a sufficient time to facilitate said solvent fractionation of a lipid composition having an increased amount of said unsaturated fatty acid esters and a decreased amount of said saturated fatty acid esters relative to said original amounts, separating a liquid fraction containing the lipid composition from a solid fraction, and isolating the lipid composition enriched in said unsaturated fatty acid esters from the liquid fraction.

17. The method of claim 16 wherein the solvent fractionation is conducted at a temperature of about −18° C. to about −38° C.

18. The method of claim 16 wherein said solvent fractionation is conducted at a temperature of about −38° C.

19. The method of claim 16 comprising the further step of separating said chicken fat into a solid phase and a liquid phase prior to mixing the liquid phase with solvent for said fractionation.

20. The method of claim 19 wherein the chicken fat is heated to an elevated temperature for liquification prior to said separation.

21. The method of claim 16 wherein said solvent fractionation is conducted at a temperature of about 0° C. to about −40° C.

22. The method of claim 16 wherein said solvent fractionation produces a liquid fraction and a solid fraction followed by separating the liquid fraction containing the lipid composition from the solid fraction by centrifugation.

23. The method of claim 22 comprising the further step of removing acetone from said lipid composition to a level fit for human consumption.

24. The method of claim 16 wherein said unsaturated fatty acid esters are selected from the group consisting of C14:1, C16:1, C18:1, C18:2, C18:3, and C20:1, and mixtures thereof.

25. The method of claim 16 wherein the monounsaturated fatty esters consist mainly of C16:1 and C18:1.

26. The method of claim 16 wherein said lipid composition has an amount of unsaturated fatty acid esters which is increased about 19% to 34% and an amount of saturated fatty acid esters which is decreased about 30% to 74%, both amounts relative to their original amounts.

27. The method of claim 26 wherein said unsaturated fatty acid esters contain monounsaturated fatty acid esters in an amount from about 16% to about 20% relative to original amounts of monounsaturated fatty acid esters in the chicken fat.

28. A lipid composition produced by the method of claim 1, 2, 3, 4, 5, 6, 7, 8, 9, 10, 11, 12, 13, 14, 15, 16, 17 or 18.

29. The method consisting essentially of the steps of claim 1.

30. The method consisting essentially of the steps of claim 6.

* * * * *